(12) United States Patent
Paldus et al.

(10) Patent No.: US 7,116,423 B2
(45) Date of Patent: Oct. 3, 2006

(54) FLOW CELL FOR OPTICAL DETECTION HAVING REDUCED SENSITIVITY TO REFRACTIVE INDEX VARIATION

(75) Inventors: Barbara A. Paldus, Sunnyvale, CA (US); Alexander Katchanov, Sunnyvale, CA (US); Robert Lodenkamper, Sunnyvale, CA (US)

(73) Assignee: Picarro, Inc., Sunnyvale, CA (US)

( * ) Notice: Subject to any disclaimer, the term of this patent is extended or adjusted under 35 U.S.C. 154(b) by 245 days.

(21) Appl. No.: 10/700,947

(22) Filed: Oct. 31, 2003

(65) Prior Publication Data

US 2005/0094158 A1    May 5, 2005

(51) Int. Cl.
*G01N 21/00*    (2006.01)
(52) U.S. Cl. ..................... 356/440; 356/246
(58) Field of Classification Search .............. 356/517, 356/432, 246, 410, 440, 519, 504
See application file for complete search history.

(56) References Cited

U.S. PATENT DOCUMENTS 6,452,680 B1*    9/2002    Paldus et al. ............... 356/436

* cited by examiner

*Primary Examiner*—Hwa (Andrew) Lee
*Assistant Examiner*—Marissa J. Detschel
(74) *Attorney, Agent, or Firm*—Lumen Intellectual Property Services, Inc.

(57) ABSTRACT

An apparatus for cavity enhanced optical detection having an improved flow cell is provided. Sensitivity of the cavity resonance condition to changes in refractive index of an analyte flowing through the flow cell is reduced. More specifically, the round trip optical path defined by the resonant cavity intersects a curved cavity input mirror at a point. This point has a location on the input mirror that is substantially independent of the refractive index of the analyte. In this manner, changes in sample refractive index do not lead to misalignment of the resonant optical cavity.

17 Claims, 8 Drawing Sheets

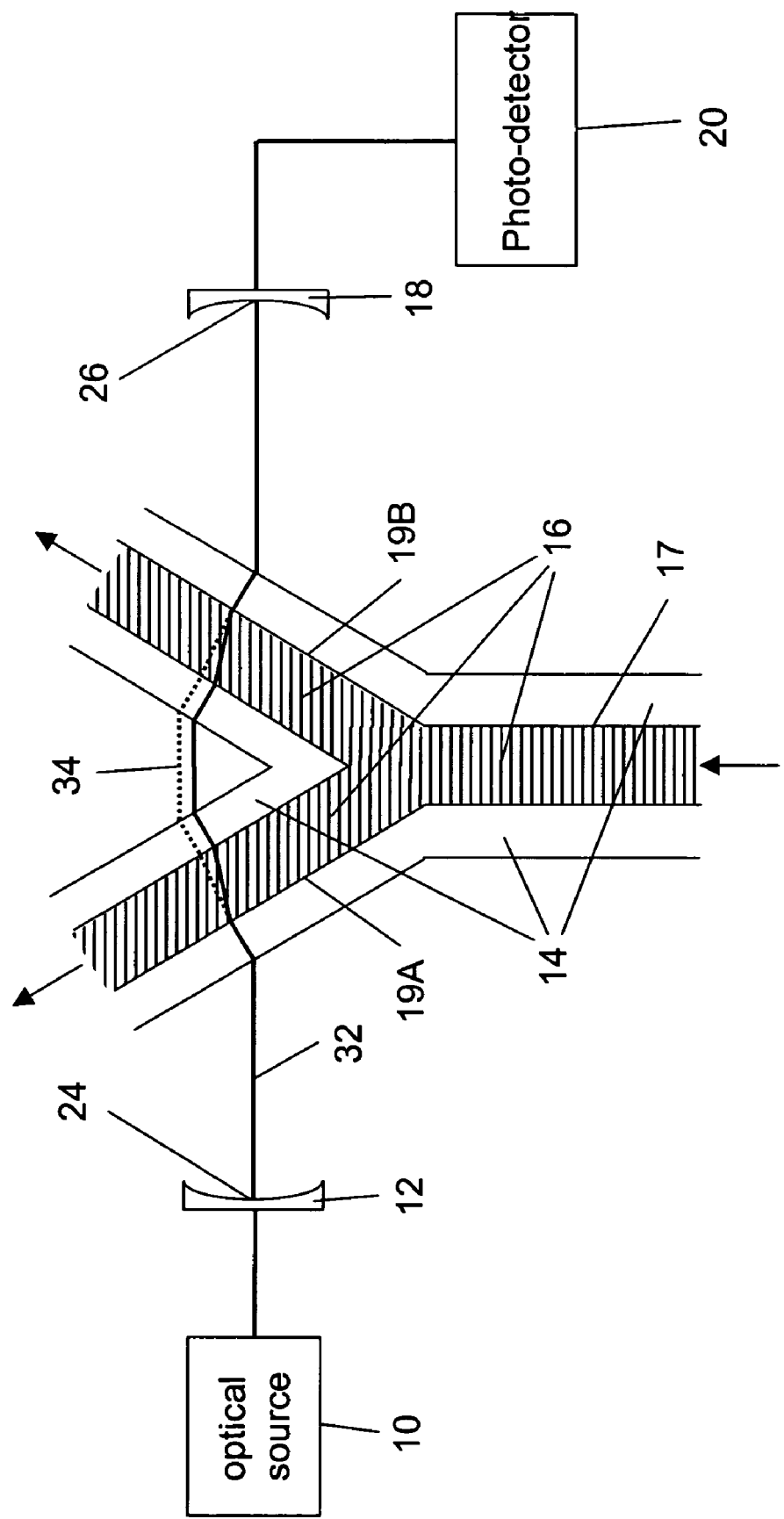

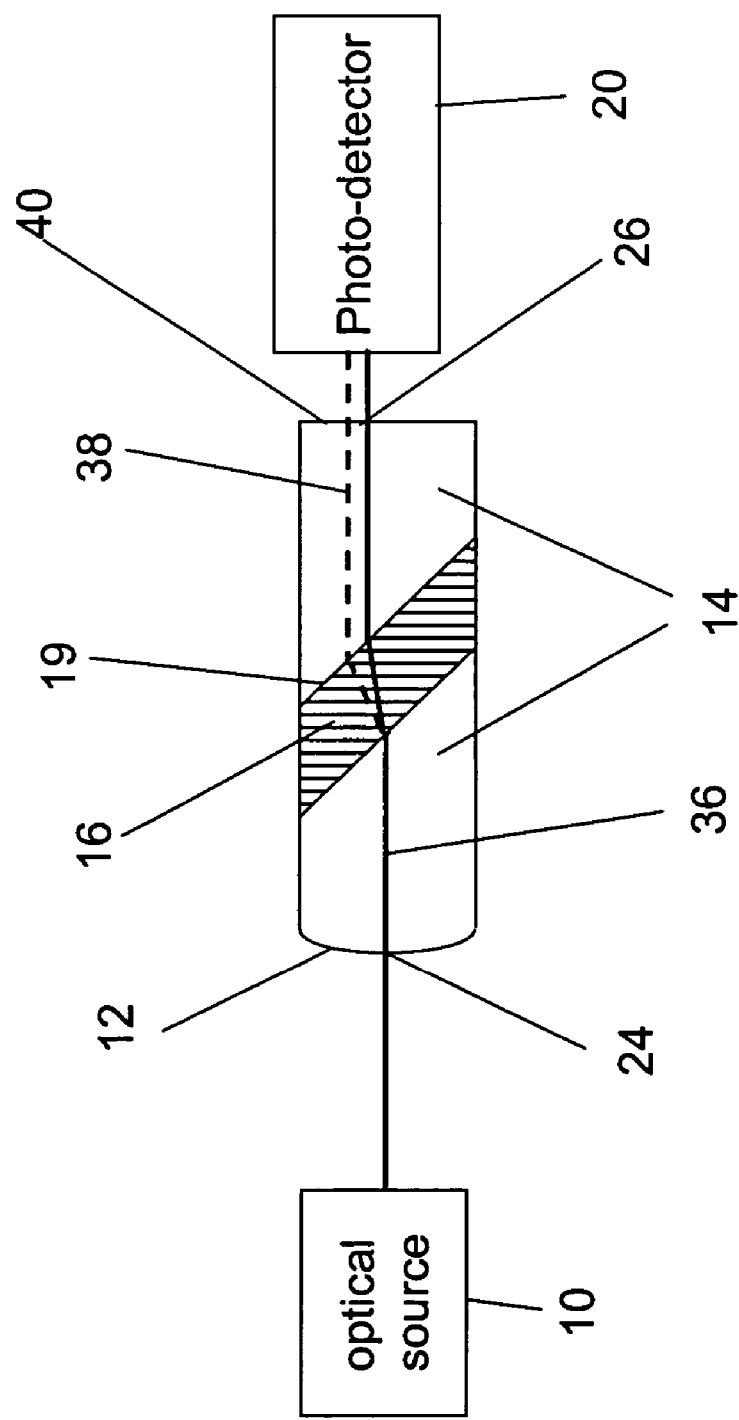

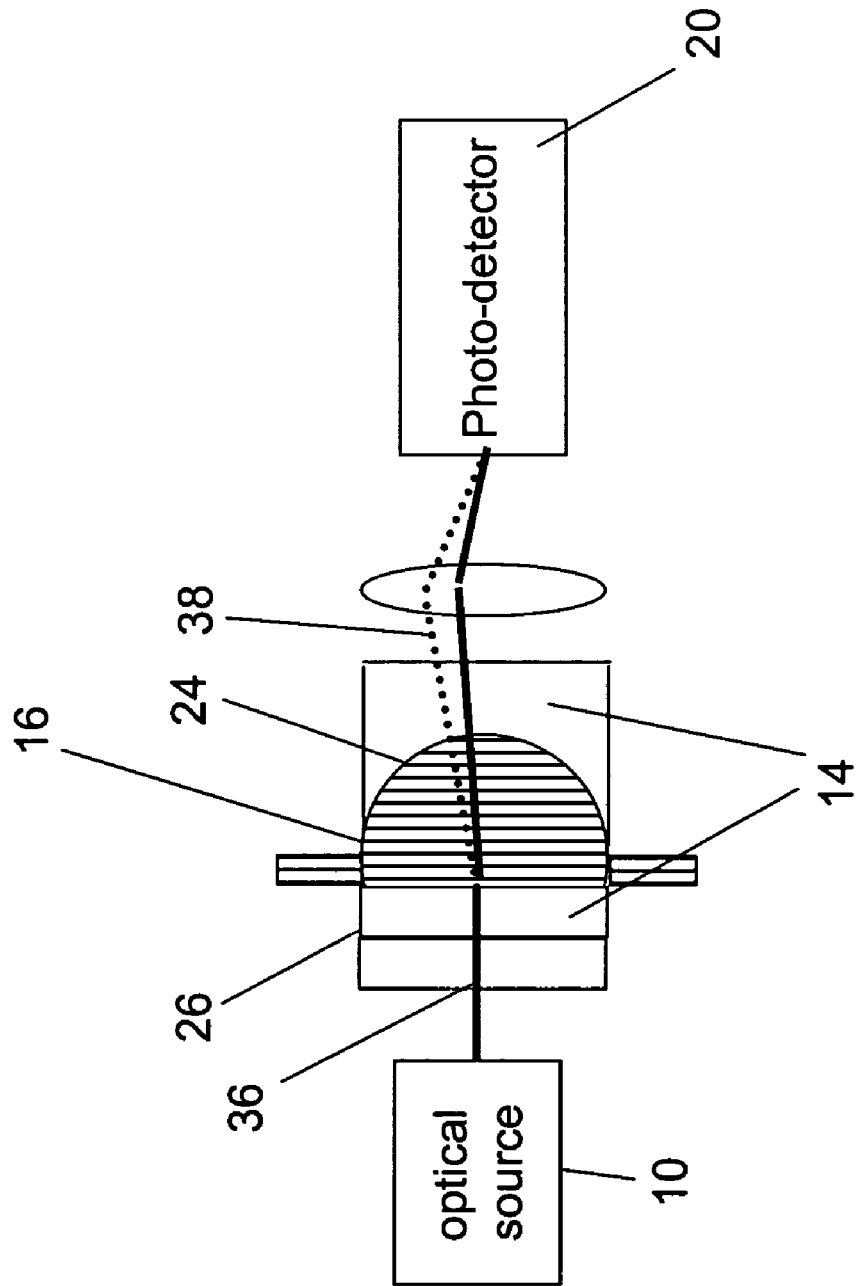

FLOW CELL FOR OPTICAL DETECTION HAVING REDUCED SENSITIVITY TO REFRACTIVE INDEX VARIATION

FIELD OF THE INVENTION

The present invention relates to optical detection, and more specifically to cavity enhanced optical detection.

BACKGROUND OF THE INVENTION

Optical detection is the determination of the presence and/or concentration of one or more target species within a sample by illuminating the sample with optical radiation and measuring optical absorption, induced fluorescence, and/or optical scattering by the sample. Optical detection has a wide variety of applications, including spectroscopy and liquid chromatography, and a correspondingly wide variety of optical detection methods are known. Cavity enhanced optical detection entails the use of a passive optical resonator, also referred to as a cavity, to improve the performance of an optical detector. Cavity enhanced absorption spectroscopy (CEAS) and cavity ring down spectroscopy (CRDS) are two of the most widely used cavity enhanced optical detection techniques.

The intensity of single-mode radiation trapped within a passive optical resonator decays exponentially over time, with a time constant $\tau$, which is often referred to as the ring-down time. In practice, it is desirable to ensure that only a single resonator mode has an appreciable amplitude, since excitation of multiple resonator modes leads to multi-exponential radiation intensity decay (i.e., multiple time constants), which significantly complicates the interpretation of measurement results. The ring-down time T depends on the cavity round trip length and on the total round-trip optical loss within the cavity, including loss due to absorption and/or scattering by one or more target species within a sample positioned inside the cavity. Thus, measurement of the ring-down time of an optical resonator containing a target species provides spectroscopic information on the target species. Both CRDS and CEAS are based on such a measurement of $\tau$.

In CRDS, an optical source is usually coupled to the resonator in a mode-matched manner, so that the radiation trapped within the resonator is substantially in a single spatial mode. The coupling between the source and the resonator is then interrupted (e.g., by blocking the source radiation, or by altering the spectral overlap between the source radiation and the excited resonator mode). A detector typically is positioned to receive a portion of the radiation leaking from the resonator, which decays in time exponentially with a time constant $\tau$. The time-dependent signal from this detector is processed to determine $\tau$ (e.g., by sampling the detector signal and applying a suitable curve-fitting method to a decaying portion of the sampled signal). Note that CRDS entails an absolute measurement of $\tau$. Both pulsed and continuous wave laser radiation can be used in CRDS with a variety of factors influencing the choice. The articles in the book "Cavity-Ringdown Spectroscopy" by K. W. Busch and M. A. Busch, ACS Symposium Series No. 720, 1999 ISBN 0-8412-3600-3, including the therein cited references, cover most currently reported aspects of CRDS technology.

Single spatial mode excitation of the resonator is also usually employed in CEAS, (sometimes called integrated cavity output spectroscopy (ICOS)), but CEAS differs from CRDS in that the wavelength of the source is swept (i.e., varied over time), so that the source wavelength coincides briefly with the resonant wavelengths of a succession of resonator modes. A detector is positioned to receive radiation leaking from the resonator, and the signal from the detector is integrated for a time comparable to the time it takes the source wavelength to scan across a sample resonator mode of interest. The resulting detector signal is proportional to $\tau$, so the variation of this signal with source wavelength provides spectral information on the sample. Note that CEAS entails a relative measurement of $\tau$. The published Ph.D. dissertation "*Cavity Enhanced Absorption Spectroscopy*", R. Peeters, Katholieke Universiteit Nijmegen, The Netherlands, 2001, ISBN 90-9014628-8, provides further information on both CEAS and CRDS technology and applications. CEAS is discussed in a resent article entitled Incoherent broad-band cavity-enchanced absorption spectroscopy by S. Fiedler, A. Hese and A. Ruth Chemical Physics Letter 371 (2003) 284–294.

In cavity enhanced optical detection, the measured ring-down time depends on the total round trip loss within the optical resonator. Absorption and/or scattering by target species within the cavity normally accounts for the major portion of the total round trip loss, while parasitic loss (e.g., mirror losses and reflections from intracavity interfaces) accounts for the remainder of the total round trip loss. The sensitivity of cavity enhanced optical detection improves as the parasitic loss is decreased, since the total round trip loss depends more sensitively on the target species concentration as the parasitic loss is decreased. Accordingly, both the use of mirrors with very low loss (i.e., a reflectivity greater than 99.99 per cent), and the minimization of intracavity interface reflections are important for cavity enhanced optical detection.

Cavity enhanced optical detection can be used for solid, liquid, aerosol, or gaseous samples. For gaseous samples, intracavity interfaces are typically not present, so there are no corresponding interface reflection losses to contribute to round trip parasitic loss. However, intracavity interfaces are typically present for solid or liquid samples. For example, contamination of the mirror surfaces by aerosols i.e., liquid and/or solid particulate containing gas samples can create problems so that these samples are generally enclosed in an intracavity cell. This cell will create interfaces (e.g., windows) within the optical resonator. Similarly, the boundaries of a solid sample are per se intracavity interfaces. Likewise, for a liquid sample contained in a flow cell present within a cavity, the interfaces between the liquid and the inner wall of the flow cell as well as the exterior wall surfaces of the flow cell are all intracavity interfaces. U.S. Pat. No. 6,452,680 teaches the minimization of intracavity reflection loss when examining solid or liquid samples by positioning the sample such that optical radiation circulating within the optical resonator is, insofar as possible, incident on the sample-induced interfaces at an angle approximating Brewster's angle and is p-polarized relative to these interfaces. Since reflection is minimized for p-polarized incidence on an interface at Brewster's angle, this arrangement significantly reduces reflection-induced parasitic loss. FIG. 1a is a schematic illustration of this cell configuration.

A variation of the design shown in FIG. 1a is shown in FIG. 1b, which design is also known to the prior art (K. Snyder and R. N. Zare, "Cavity Ring-down Spectroscopy as a Detector for Liquid Chromatography" Analytical Chemistry, Vol. 75, p 3086–3091 (2003). In this design the liquid flow channel is tilted within the cell so that the light beam strikes each surface at the correct Brewster's angle for the specific interface (e.g. air→fused silica→liquid→fused silica→air). With the appropriate polarization of light, the interface reflections are minimized, thereby allowing the light to pass back and forth through the cell multiple times, resulting in a relatively long ring-down constant. In the example shown in FIG. 1b, using a fused silica cell and water as the sample liquid, angle e is 7.9° and angle a is 55.6° so that the light refracts through the cell, hitting each interface surface at approximately Brewster's angle for minimum reflection. The system shown in FIG. 1b provides some advantage relative to the arrangement of FIG. 1a in that by tilting the flow channel within the cell the light path is incident on all interfaces at approximately Brewster's angle.

However, the arrangements shown in FIGS. 1a and 1b both suffer from a drawback in that a change in the refractive index of the sample can cause the cavity to become misaligned and potentially unstable. A detailed discussion of cavity stability can be found in Chapters 19 and 20 of "Lasers" by A. E. Sigman, University Science Books Sausalito, Calif., 1986. Variability of the sample refractive index is especially pertinent for liquid chromatography applications, since the sample refractive index will frequently change as a separation proceeds, especially in the many cases where it is desirable to use various solvents having different refractive indices to perform sequential or different separations in the same instrument. In addition, variation of sample temperature and/or pressure can also cause changes in the sample refractive index. This same analysis applies to the situation where the light source wavelength $\lambda_s$ is changed from the original design wavelength to $\lambda_d$ ($\lambda_d \neq \lambda_s$) In this case the light will travel along different paths in both the flow cell (e.g.,glass) and the fluid sample. This is a significant limitation if it is desired to use the system with a broadband or tunable source of radiation.

SUMMARY OF THE INVENTION

It is an object of the present invention to provide an apparatus for cavity enhanced optical detection having reduced sensitivity to variation of the sample refractive index. A further object of the invention is to provide both reduced sensitivity to variation of sample refractive index and reduced parasitic loss. Another object is to provide an apparatus which is suitable for detection of a variety of samples using a variety of optical radiation sources. Suitable sources include a tunable laser (i.e., a laser whose wavelength is variable over time) or a fixed frequency laser either of which can be pulsed or continuous wave, or a broadband incoherent light source, such as a LED, without resulting in a misaligned or unstable cavity. The apparatus of the present invention is suitable for use in both CRDS and CEAS instruments.

The present invention comprises an optical detector for cavity enhanced optical detection having an optical resonator where the optical alignment of the resonator is unaffected by changes in the refractive index of a sample or sample cell present within the resonator or in the excitation source wavelength. Changes in a sample refractive index can be caused by among other things changes in sample chemical composition and/or concentration. More specifically, the optical alignment of the resonator is unaffected by changes in the sample refractive index if two conditions are satisfied: (i) the resonator, including the sample, has a round trip radiation path for at least two different values of the sample refractive index; and (ii) the round trip radiation path within the resonator remains aligned with respect to the optical source illuminating the resonator. Since one of the resonator mirrors is an input mirror which receives radiation from the optical source, condition (ii) above can be restated as a requirement that the location of the point where the round trip radiation path impinges on the input mirror and the angle of incidence of the beam at that point be substantially insensitive to changes in the sample refractive index. The same is true for the wave length of the source radiation. Although the round trip path length of some embodiments of the present invention can change if the wavelength of the laser changes, our design (unlike the prior art designs shown in FIGS. 1a and 1b) ensures that the cavity alignment and stability are preserved even if the laser wavelength and/or the refractive index of the sample changes.

In a first preferred embodiment of the invention as shown in FIG. 2, a fluid sample is contained within a flow cell having a generally Y-shaped fluid flow path. In other words, fluid enters an input channel (the base of the Y) and the fluid flow is then split into two analysis channels (the branches of the Y) which intersect the round trip radiation path at substantially equal but opposite angles. As a result of this arrangement of the analysis channels, the net lateral displacement (if any) of an optical beam upon passage through both analysis channels is unaffected by the sample refractive index. In other words, the locations of the points where the round trip radiation path impinges on each of the two resonator mirrors are substantially unaffected by changes in the sample refractive index thereby maintaining cavity alignment.

In a second preferred embodiment of the invention, a flow cell having a single analysis channel intersecting the round trip radiation path is employed in a cavity, having a first curved input mirror and a planar second mirror. Although the lateral displacement of an optical beam passing through such a flow cell depends on the sample index of refraction, displacement of the beam does not lead to misalignment of the cavity, since in this embodiment the planar mirror is aligned to retroreflect the beam. The location of the point at which the round trip radiation path impinges on the input mirror is thus substantially insensitive to changes in the sample refractive index or the laser wavelength, as further explained in the detailed discussion of FIGS. 3a and 3b.

A third preferred embodiment of the invention as shown in FIG. 4 is conceptually similar to the configuration shown in FIG. 3a except that in this embodiment the concave and planar mirrors are integral with the opposing faces of the flow cell.

A further embodiment of the invention is shown in FIG. 5 wherein a combination of two planar mirrors and single concave mirror in conjunction with a prism is used to provide a ring cavity which likewise prevents changes in a sample's refractive index or the laser wavelength from causing cavity misalignment.

As used in the present specification and in the appended claims, the term "fluid" is intended to encompass both liquids and aerosols (suspensions of micro particles of liquids and/or solids in a gas, e.g., air). The present invention is particularly useful for the spectroscopic analysis of aqueous or methanol eluent solutions from liquid chromatography columns and also of atmospheric samples which comprise aerosols. In each of these cases the composition of the fluid sample can vary significantly during the course of an analysis.

BRIEF DESCRIPTION OF THE DRAWINGS

FIG. 2 schematically shows a first embodiment of a cavity enhanced optical detector according to the present invention.

FIGS. 4 and 5 show two additional embodiments of the present invention which, even as the designs shown in FIGS. 2, 3a and 3b, maintain the optical alignment of the resonator notwithstanding changes in the refractive index of the liquid test sample.

FIG. 4 uses one concave and one planar mirror even as the embodiments of FIGS. 3a and 3b, however in this case the two mirrors are integral with the flow cell front (curved) and rear (planar) surfaces, respectively.

FIG. 5 shows a ring cavity embodiment of the invention using two planar mirrors and one concave mirror.

FIG. 6 shows another embodiment of the invention.

DETAILED DESCRIPTION OF THE DRAWINGS

In each of the figures like numbers denote the same or functionally equivalent components.

Figure 1A:
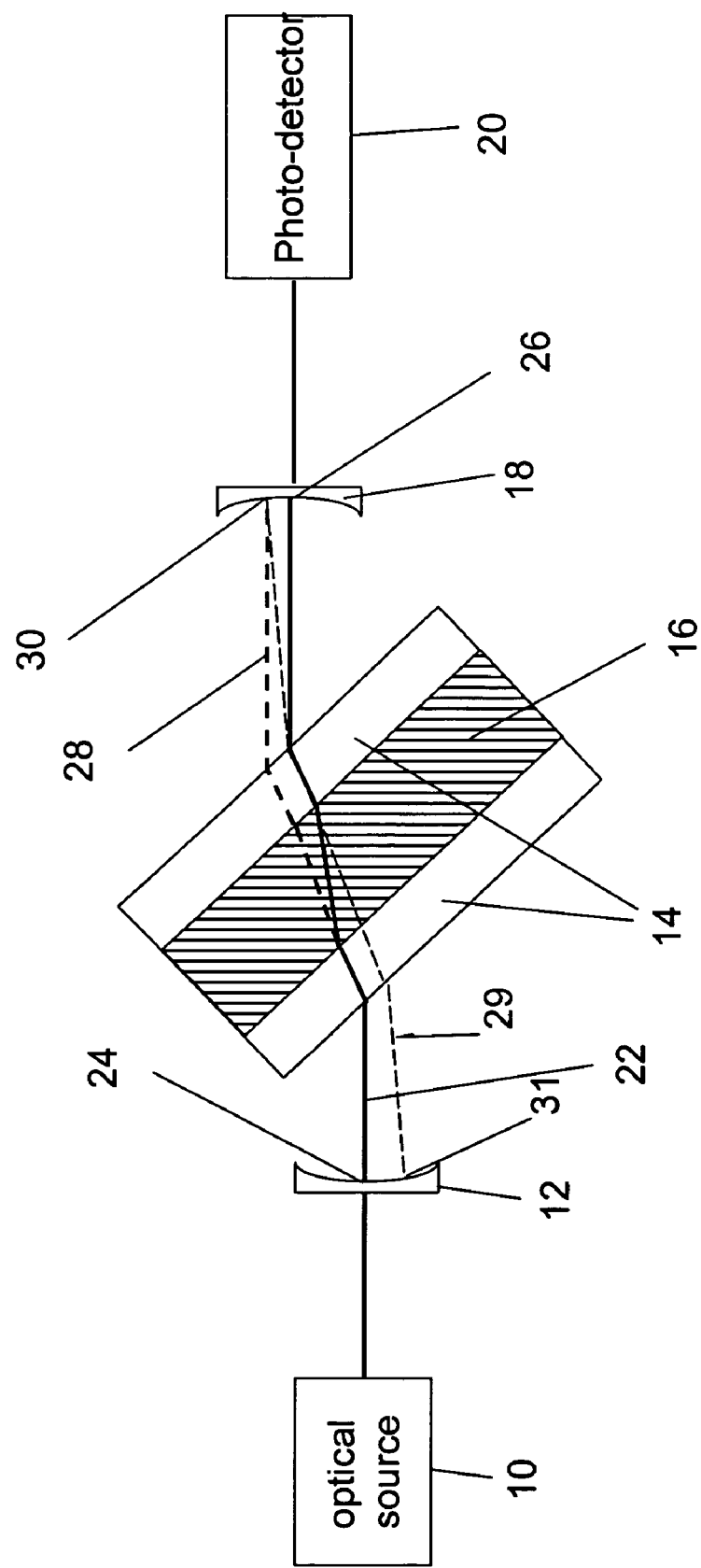
FIGS. 1a and 1b schematically show two similar prior art designs for a cavity enhanced optical detector.

FIG. 1a schematically shows a cavity enhanced optical detector according to U.S. Pat. No. 6,452,680. Optical source 10 provides radiation which is received by mirror 12, and a portion of the received radiation is coupled into the optical cavity (resonator) formed by mirrors 12 and 18, and including flow cell 14 containing sample 16 having a refractive index $n_1$. As explained by Siegman in Chapter 19 of his previously referenced book, the optical resonator of FIG. 1 is a stable resonator, if the radii of curvature (R12 and R18) of mirrors 12 and 18, respectively, satisfy the stability condition:

$$0 \leq (1-L/R12)(1-L/R18) \leq 1, \quad (1)$$

where L is the diffractive optical distance between point 24 on mirror 12 and point 26 on mirror 18. The diffractive optical distance between any two points is the integral of $L_{mat}/n_{mat}$ where $L_{mat}$ is the length of the physical optical path connecting the two points, and where $n_{mat}$ is the index of refraction of the material through which the optical beam is passing (which, in the cavity shown, will vary along the optical path). More particularly for the design shown in FIG. 1a $$L = 2L_{air}/n_{air} + 2L_{glass}/n_{glass} + L_{sample}/n_{sample}$$

where each L is distance the light passes through air, glass and the sample, respectively, divided by the corresponding refractive index of each of the materials, i.e. air, glass or sample, respectively. As shown, the beam passes through two different air and glass segments which is the reason the above equation for L includes the multiple 2 for these two segments of the cavity. Also, note that the refractive index of air, glass and the sample are all affected by the wavelength of the incident light but that only the sample index is affected by the sample composition (including the concentration of target species), temperature, and pressure.

Radiation circulates within the resonator along round trip radiation path 22 (solid line), which impinges on mirrors 12 and 18 at points 24 and 26 respectively. A portion of the circulating radiation which impinges on mirror 18 is transmitted through mirror 18 and is received by photodetector 20. According to the teaching of U.S. Pat. No. 6,452,680, the interfaces between sample 16 and flow cell 14, and/or the wall surfaces of flow cell 14, are configured to intersect path 22 at substantially Brewster's angle to reduce round trip loss within the cavity.

If the index of sample 16 is $n_1$, then light circulating within the resonator formed by mirrors 12 and 18 follows path 22, and the resonator is aligned to the input beam (since path 22 is aligned with the axes of mirrors 12 and 18). If the refractive index of sample 16 is changed to a value $n_2$, which differs from $n_1$, then light inside the cavity will follow a different path. In this case a round trip light path, if one exists, is no longer aligned with the axes of mirrors 12 and 18, which, at the least, increases parasitic round trip loss because the beam incidences at the interfaces will no longer be at substantially Brewster's angle. In the example of FIG. 1a, with sample 16 having a refractive index $n_2$ different from $n_1$, light traveling from mirror 12 to mirror 18 follows path 22 (solid line) until it reaches the first interface between the inner wall surface of flow cell 14 and sample 16. At that point the beam is refracted through a different angle than the angle of path 22, since the angle of refraction between flow cell 14 and sample 16 for non-normal incidence depends on the refractive index of sample 16. Therefore, the beam follows path 28 (dotted line), which is distinct from path 22, to mirror 18. Path 28 impinges on mirror 18 at point 30, which is different from point 26. Path 22 is aligned with the axis of mirror 18, as indicated on FIG. 1a (or 1b), while path 28 is parallel to path 22 but offset from it. Therefore path 28 cannot be aligned with the axis of mirror 18 and does not impinge on mirror 18 at point 26 but rather at point 30. Since path 28 is not aligned with the axis of mirror 18 its return path to mirror 12 will not coincide with path 22 but will rather proceed along a different path 29 and will impact mirror 12 not at point 24 but rather at some different point e.g. 31, thereby rendering the cavity misaligned with respect to the input beam. This, at the very least, undesireably increases parasitic round trip loss and, if the misalignment is large, can render the cavity unstable because of walk-off along the mirrors 22 and 18. In a a severe case, the cavity may be rendered unstable because of walk-off along the mirrors 12 and 18.

Figure 1B:
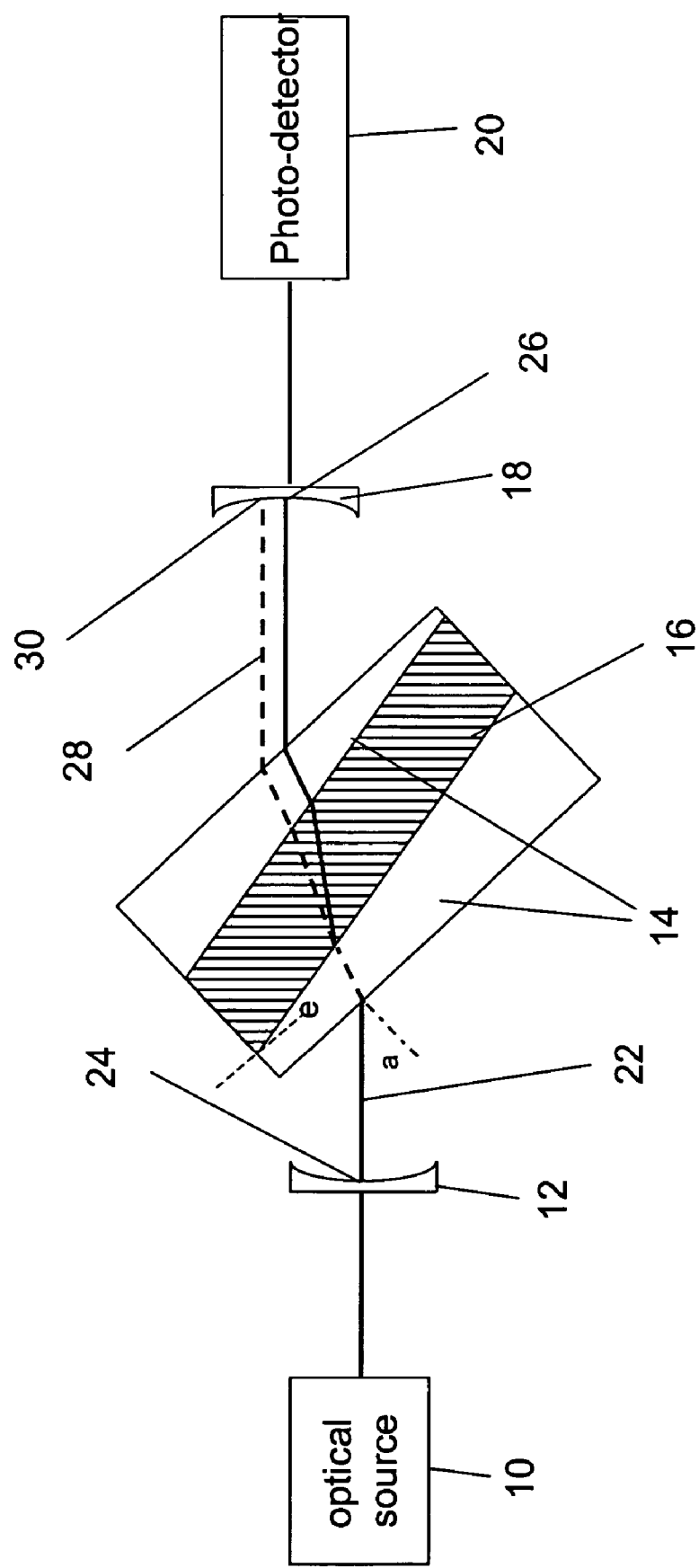

FIG. 1b illustrates another prior art attempt at reducing intracavity reflections by making all light incident angles approach Brewster's angle. The same numbers in both FIGS. 1a and 1b denote the same components. Angle "a" would be the same for FIG. 1a or 1b, that is the air→first flow cell wall interface. However angle e enables the incident light after passing through the sample to also impinge on the second (opposite, interior) flow cell wall surface at Brewster's angle. As used herein, the first flow cell wall is the wall closest to the source of optical radiation and the second, as discussed above, is the wall distal the light source.

In the configuration of both FIGS. 1a and 1b varying the refractive index of the sample will only affect the glass→liquid interface and not alter the fact that the air→flow cell wall interface remains at Brewster's angle. However, in the design of either FIG. 1a or 1b, a change in the sample refractive index will tend to misalign the cavity with respect to the fixed input beam path 22. Moreover, if the wavelength of the source laser or other light source changes, all interfaces will tend to deviate from Brewster's angle because the glass and liquid are usually dispersive. Thus the designs of FIGS. 1a and 1b are realistically suitable only for an instrument where little variation occurs in both the sample refractive index and the source light wave length. Although the cavity design shown in FIG. 1b reduces intracavity reflections it does not solve the problem of cavity misalignment resulting from a change in sample refractive index.

A correctly aligned cavity round trip path for the examples of FIGS. 1a and 1b will frequently not exist when the sample index is $n_2$. Of course, the cavity alignment could be adjusted for use with a sample having a refractive index $n_2$ by repositioning (translating) mirror 18 such that its axis is aligned with path 28 on FIG. 1a, but then the cavity would be misaligned for a sample having a different refractive index (e.g., $n_1$).

Thus the arrangements of both FIGS. 1a and 1b suffer from the drawback that the round trip cavity parasitic loss can significantly increase due to changes in cavity alignment induced by changes in sample refractive index. The same arguments about cavity misalignment can be made if the system is designed at wavelength $\tau_d$ but is operated at a different wavelength $\tau_s$. In this case path 28 will deviate from path 22 within both the flow cell walls and the sample. This new path may not even be parallel to path 22.

FIG. 2 schematically shows a first embodiment of the present invention which overcomes an inherent drawback of the arrangement of FIGS. 1a and 1b. Optical source 10 provides radiation which is received by input mirror 12, and a portion of the received radiation is coupled into the optical cavity (resonator) formed by concave mirrors 12 and 18. Optical source 10 can be either a coherent light source (e.g., a pulsed or CW laser) or an incoherent light source (e.g., a lamp or a light emitting diode). Note that the same light sources are also suitable for the other embodiments of the present invention. The optical resonator of FIG. 2 is a stable resonator as defined by Siegman, where the radii of curvature R12 and R18, of mirrors 12 and 18 respectively, satisfy the stability condition:

$$0 \leq (1-L/R12)(1-L/R18) \leq 1, \quad (2)$$

where L is the diffractive optical distance between point 24 on input mirror 12 and point 26 on mirror 18 on FIG. 2. Mirrors 12 and 18 preferably each provide high reflectivity (i.e., reflectivity $R \geq 0.95$) and low loss (i.e., $R+T \geq 0.995$, where T is the transmissivity).

Radiation circulates within the resonator along round trip radiation path 32 (solid line), which impinges on mirrors 12 and 18 at points 24 and 26, respectively. A portion of the circulating radiation which impinges on mirror 18 is transmitted through mirror 18 and is received by photodetector 20. Photodetector 20 is preferably a semiconductor (photodiode) photo-detector, responsive to the radiation provided by optical source 10. Flow cell 14, which is generally Y shaped, comprises a fluid input channel 17 and two analysis channels 19A and 19B (the two arms of the Y). Analysis channels 19A and 19B are in fluid communication with input channel 17 so that the flow of fluid sample 16, having a refractive index $n_1$, within input channel 17 is divided into two flows through both analysis channels 19A and 19B, as indicted by the arrows. Each analysis channel intersects round trip radiation path 32 at angles of intersection that are equal, or approximately equal, to each other (although of opposite sign) and also approximately (i.e., within ±5 degrees of) Brewster's angle.

If the refractive index of sample 16 is changed to a value $n_2$ which differs from $n_1$, then light input to the cavity will follow a different path. In the embodiment of FIG. 2, if sample 16 has a refractive index $n_2$, different from $n_1$, light traveling from mirror 12 to mirror 18 will again follow path 32 (solid line) until it reaches the first interface between flow cell 14 and sample 16, i.e., at analysis channel 19A. At that point, the beam is refracted through a different angle than the angle of path 32, since the angle of refraction between flow cell 14 and sample 16 for non-normal incidence depends on the refractive index of sample 16. Therefore, the beam follows path 34 (dotted line), which will be different from path 32. However, the arrangement of the analysis channels 19A and 19B of FIG. 2 is substantially symmetrical, so that the difference between paths 32 and 34 introduced by analysis channel 19A is eliminated (compensated for) upon passage through analysis channel 19B, as shown on FIG. 2. Round trip radiation path 34 (even as path 32) will impinge on mirrors 12 and 18 at points 24 and 26, respectively, and is aligned with the mirror axes. Thus this flow cell configuration ensures that the locations of the points where the round trip radiation path impinges on the two resonator mirrors are substantially insensitive to changes in the sample refractive index.

Since the alignment of the round trip radiation path to mirrors 12 and 18 is substantially insensitive to changes in the refractive index of sample 16, the resonator misalignment drawback of the arrangement of FIGS. 1a and 1b is avoided. However, round trip path 34 has a different diffractive length than round trip path 32, so for a practical instrument according to the embodiment of FIG. 2, one should ensure that the stability condition of Equation 2 is satisfied for round trip paths corresponding to the range of sample refractive indices and/or light source wavelengths expected in applications of the instrument. In this design, if the wavelength of the light source is changed from the design wavelength, again the light will follow a different path from path 32, with the flow cell walls contributing a different refractive path. However, in this case as well, the symmetric geometry of the flow cell arms will compensate for these deviations, resulting in an optical beam that continues to impinge on mirror 18 at point 26.

Figure 3A:
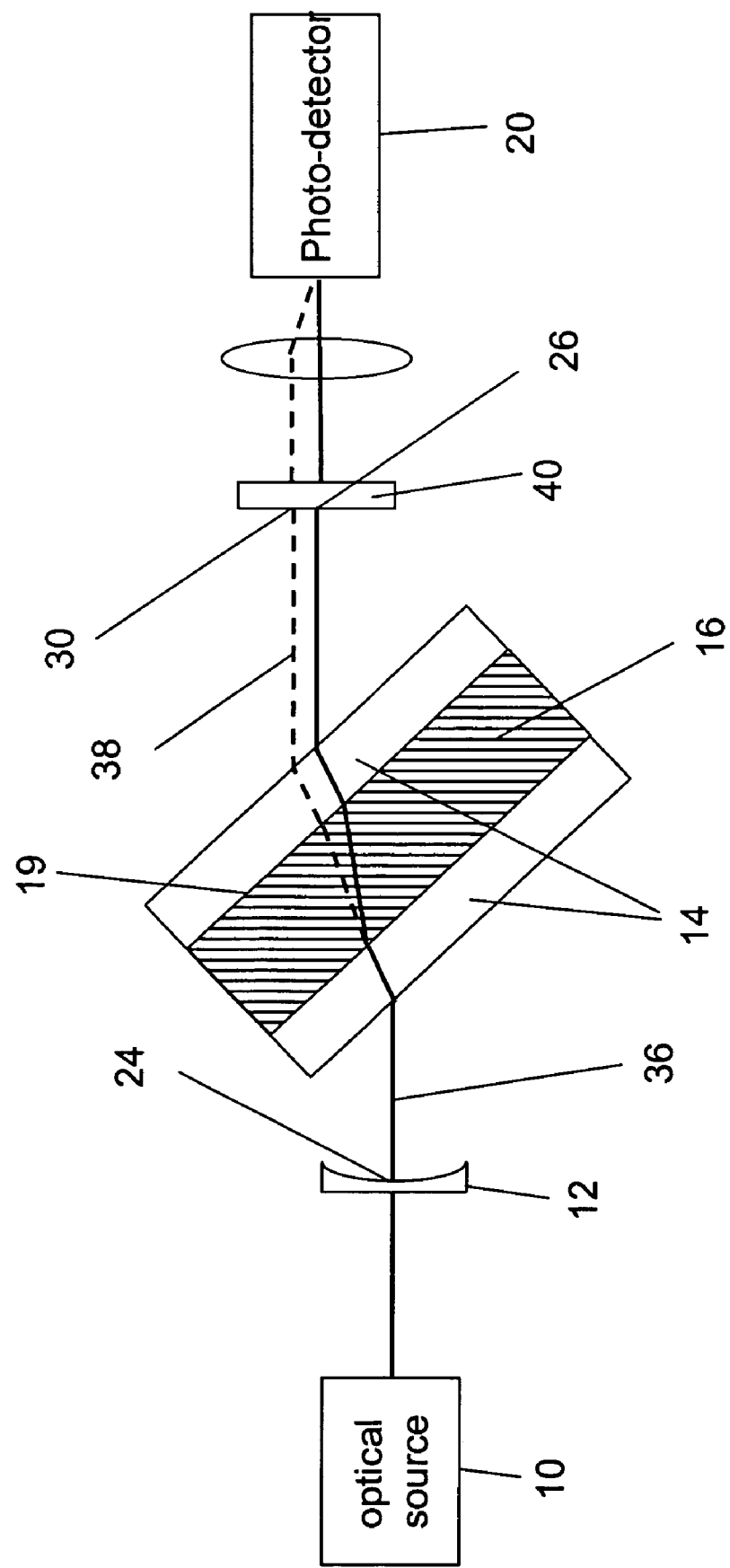
FIGS. 3a and 3b schematically show a second embodiment of a cavity enhanced optical detector according to the present invention using one concave and one planar mirror to achieve the desired retention of beam alignment.
Figure 3B:
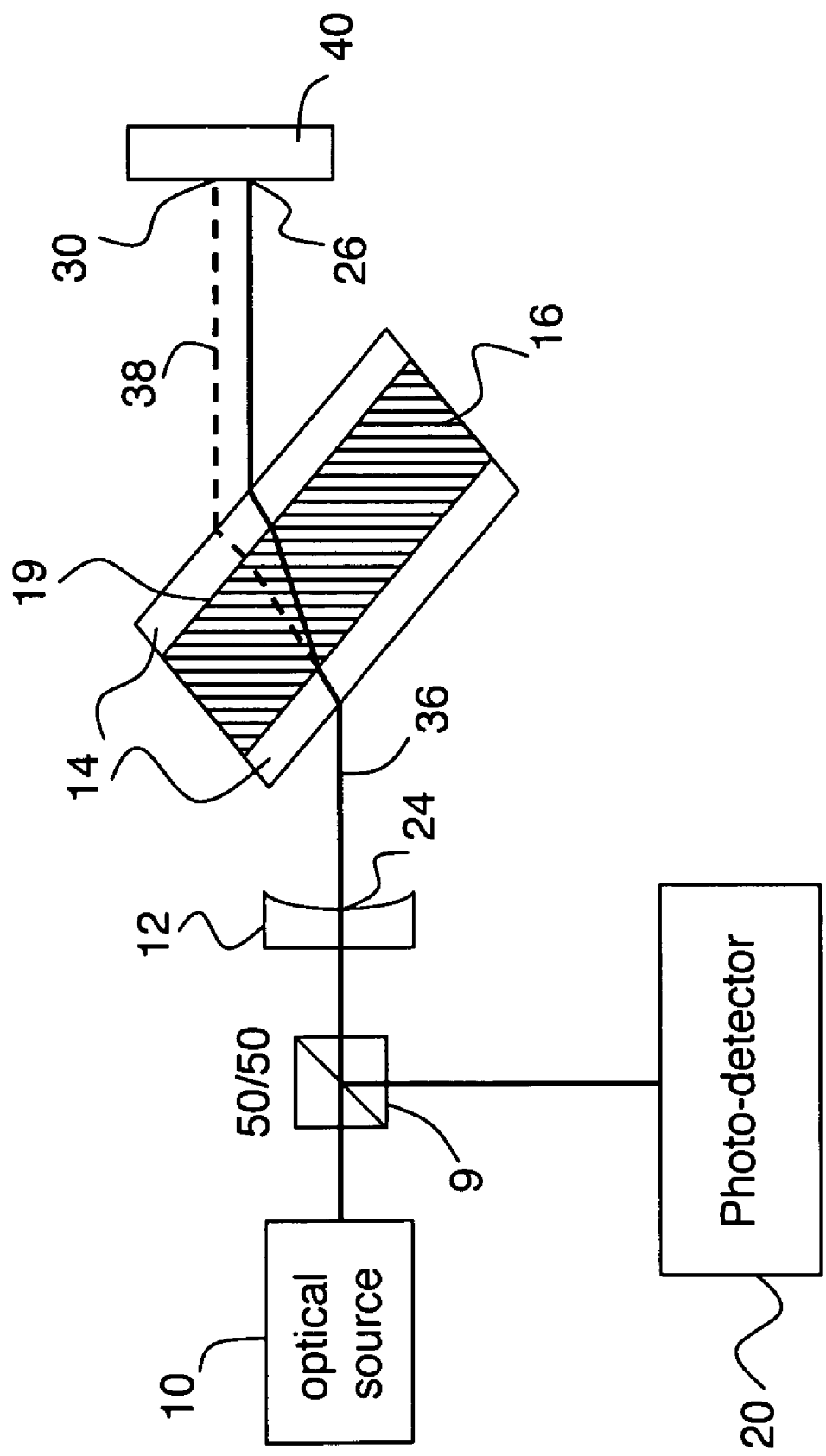

FIGS. 3a and 3b schematically show a second embodiment of the present invention which also overcomes the drawback of the arrangement of FIGS. 1a and 1b. In FIG. 3a optical source 10 provides radiation which is received by input mirror 12, and a portion of the received radiation is coupled into the optical cavity (resonator) formed by mirrors 12 and 40. Optical source 10 can be either a coherent light source (e.g., a pulsed or CW laser which is generally preferable) or an incoherent light source (e.g., a lamp or a light emitting diode together with a wavelength selection filter). Mirror 40 is a substantially planar mirror. The optical resonator of FIGS. 3a (and 3b) is a stable resonator, where the radius of curvature R12 of input mirror 12, satisfies the stability condition:

$$0 \leq (1-2L'/R12) \leq 1, \quad (3)$$

where L' is the diffractive optical distance between point 24 on input mirror 12 and point 26 on mirror 40 on FIG. 3. Mirrors 12 and 40 preferably each provide high reflectivity (i.e., reflectivity $R \geq 0.95$) and low loss (i.e., $R+T \geq 0.995$, where T is the mirror transmissivity).

Radiation circulates within the resonator along round trip radiation path 36 (solid line), which impinges on mirrors 12 and 40 at points 24 and 26, respectively. A portion of the circulating radiation which impinges on mirror 40 is transmitted through mirror 40 and is received by photodetector 20. Photodetector 20 is preferably a semiconductor photodetector or photomultiplier, responsive to the radiation provided by optical source 10. Sample 16, having a refractive index $n_1$, flows within flow cell 14, which includes an analysis channels 19. Analysis channel 19 preferably intersects round trip radiation path 36 at an angle of intersection that is equal to, or approximately equal to, (i.e., within ±5 degrees of) Brewster's angle.

If the refractive index of sample 16 is changed to a value $n_2$ which differs from $n_1$, or if the wavelength of the light source changes then light inside the cavity will follow a different path. In the embodiments of FIGS. 3a and 3b, with the refractive index of sample 16 being changed to $n_2$ (different from $n_1$), light traveling from mirror 12 to mirror 40 will follow path 36 (solid line) until it reaches the first interface between flow cell 14 and sample 16, which is associated with analysis channel 19. At that point, the beam is refracted through a different angle than the angle of path 36, since the angle of refraction between flow cell 14 and sample 16 for non-normal incidence depends on the refractive index of sample 16. Therefore, the beam follows path 38 (dotted line), which is distinct from path 36. Round trip radiation path 38 is offset but parallel to path 36 and impinges on mirror 40 at point 30, which is spaced apart from point 26. However, since mirror 40 is substantially planar and retroreflecting, the optical resonator formed by mirrors 12 and 40 is not misaligned for sample 16 having a refractive index $n_2$ different from $n_1$. The lateral displacement of a beam (e.g., the separation of the point of impact of paths 36 and 38 at mirror 40, i.e., 26 and 30) avoids resonator misalignment if mirror 40 is substantially planar. Note, however, that the changing position of the output beam can sometimes become a problem for the collection optics which might have to be realigned in some cases.

The configuration shown in FIG. 3b differs somewhat from that shown in FIG. 3a, although the fundamental approach to overcoming the effect of a change in sample refractive index is the same. In the embodiment shown in FIG. 3b a 50/50 beam splitter 9 is interposed between the optical source 10 and the input mirror 12. The light which is reflected back from mirror 40 and then through mirror 12 is then one-half of the reflected light. It is directed by the beam splitter 9 into photo-detector 20. It should be noted that this alternative arrangement, entailing the use of a beam splitter interposed between the optical source and the input lens, is also applicable to the instrument configuration shown in FIG. 4. This embodiment solves the motion problem of the output beam relative to the detector because it collects light from point 24, which remains invariant to changes in either sample index or excitation wavelength.

An arrangement similar to the embodiment of FIGS. 3a and 3b, except that the roles of the two mirrors is reversed (i.e., the input mirror is planar, and the second mirror is curved) is operable, although not preferred. The reason for this is that the intracavity round trip path impinges on the planar mirror at various points, depending on the sample refractive index, and this variation in the cavity round trip path will cause the input beam to not always be aligned to the cavity. Although it is possible to provide means for translating the beam of radiation provided by source 10 to maintain alignment of source to cavity as the sample refractive index is varied, such an arrangement is unnecessarily complicated. In the embodiment shown in FIGS. 3a and 3b, the alignment of the light source with the cavity is provided by the consistency of the location of point 24 notwithstanding changes in sample refractive index or excitation wavelength.

Since a round trip radiation path exists for varying values of the sample refractive index, and the alignment of the round trip radiation path to input mirror 12 is insensitive to changes in the refractive index of sample 16, the resonator misalignment drawback of the arrangement of FIGS. 1a and 1b is avoided. However, round trip path 38 has a different diffractive length than round trip path 36, so for a practical instrument according to the embodiment of FIGS. 3a and 3b, it is important to ensure that the cavity stability condition of Equation 3 is satisfied for round trip paths corresponding to the range of sample refractive indices and light source wavelengths expected in applications of the instrument. Note that the optical cavity configurations of the present invention shown in FIGS. 2, 3a and 3b can benefit in terms of reduced reflectivity by using a cell configuration of the type shown in FIG. 1b (i.e. both the exterior wall of the flow channel proximal the optical source and the interior distal wall surface intersect the radiation path at approximately Brewster's angle).

FIG. 4 illustrates a preferred embodiment wherein curved mirror 12 and planar mirror 40 (the input and output mirrors, respectively) form the end faces of an integral resonator structure which includes the fluid flow channel. Again the optical beam 36 will preferably intersect the wall of the flow cell at an angle approximately equal to Brewster's angle. Cell 14, as in other embodiments of the invention, will normally be fabricated from quartz, fused silica, BK7 glass or a similar transparent material. In the design shown in FIG. 4, the mirrors will normally be formed on the outer cell surface by known techniques such as sputtering or chemical vapor deposition. An advantage of the configuration shown in FIG. 4 is that there are no air to flow cell wall interfaces. Hallock et al, Anal. Chem. 2002, 74, 1741–1743 have used an approach in which they filled the entire ring-down cavity with a sample liquid of interest, thereby allowing the liquid to actually contact the mirrors. This approach has been applied to kinetic studies, but is not suitable for the analysis of small volumes of liquid owing to the inherently short ring-down life times resulting from the necessarily extremely close mirror separation. Furthermore, in this design, the length of the flow cell, and hence sample absorption losses cannot be matched to the mirror optical losses. The optical resonator of FIG. 4 is a stable resonator, where the radius of curvature R12 of input mirror 12, satisfies the stability condition:

$$0 \leq (1 - 2L'/R12) \leq 1 \tag{4}$$

where L' is the diffractive optical distance between point 24 on input mirror 12 and point 26 on mirror 40.

Figure 5:
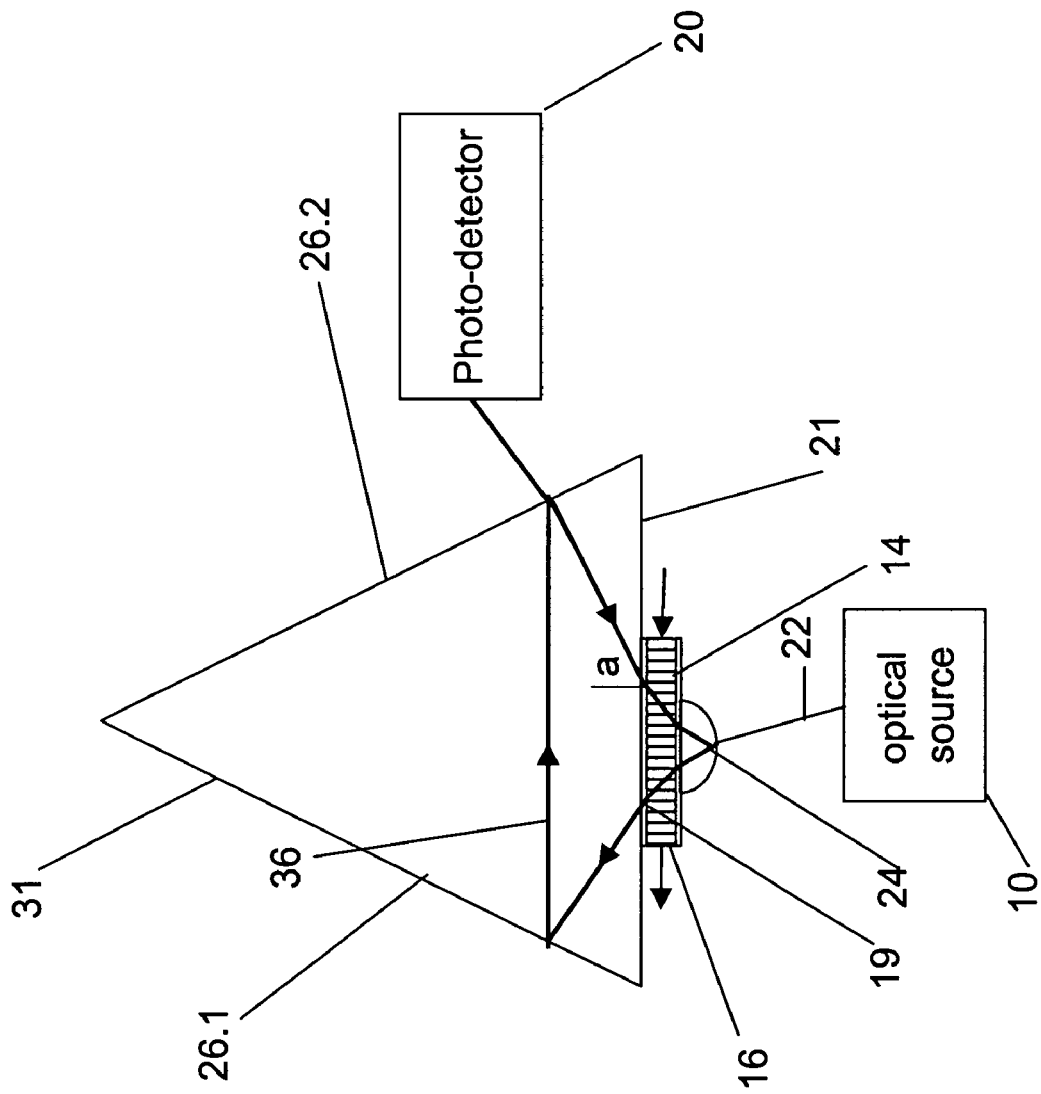

FIG. 5 shows an additional embodiment of the present invention wherein a ring cavity configuration using a prism is utilized to provide a stable optical resonator which accommodates changes in the refractive index of sample 16 passing through analysis channel 19 of flow cell 14. In this design optical source 10 inputs a light beam along path 22 through concave mirror 24. It passes through optical channel 19 and is refracted as shown. Faces 26.1 and 26.2 of prism 31 are coated over at least that portion of their surface on which the light beam impinges, to provide mirrors having high reflectivity. Optical channel 19 is positioned relative to the third surface 21 of prism 31 so that the angle shown as a approximates Brewster's angle so as to permit maximum transmission of the optical beam reflected from prism face 26.2 into analysis channel 19. The direction of flow of sample 16 can be either transverse as shown by the arrows at the right and left sides of channel 19 or in a direction perpendicular into the plane of FIG. 5. As indicated, radiation path 36, after reflection by prism face 26.2, impinges on the wall of analysis channel 19 at approximately Brewster's angle. As shown in FIG. 5, the radiation is refracted both on its initial passage through the flow cell and then on its return path through the flow cell to concave mirror 24 which provides the third reflecting surface of the ring cavity. Mirror 24 is centered on, and perpendicular to, the axis of symmetry of prism 31. The beam is reflected by reflective surface 26.2 through prism face 21 and thence through the flow cell whereby the initial refraction is reversed, in effect achieving the same result as obtained by the double pass arrangement shown in FIG. 2. Although a change in the refractive index of sample 16 will alter the path of beam 36 on its first contact with the interface between flow cell 14 and sample 16, this path alteration will be recovered when the beam is reflected back through the flow cell by mirror 26.2. As shown, a portion of the circulating radiation which impinges on reflective surface 26.2 is transmitted through this surface and is received by photo-detector 20.

The requirement for a stable resonator with two concave mirrors having the same radius of curvature is $0 \leq 1-L/R \leq 1$ where L is the distance between the two concave mirrors. If the two concave mirrors have a different radius of curvature the requirement can be expressed as $0 \leq (1-L/2R')(1-L/2R'') \leq 1$ where R' is the radius of curvature of the input mirror and R'' is the radius of curvature of the output mirror In both cases L is the diffractive optical distance between the point on the input mirror where the light enters the resonant cavity and the point at which it impinges on the facing concave output mirror.

Where, as in the design shown in FIGS. 3a, 3b and 4, there is one concave and one planar mirror the requirement for cavity stability can be expressed as $0 \leq (1-L'^{rt}/R^1) \leq 1$ where $R^1$ is the radius of curvature of the input mirror and $L'^{rt}$ is twice the diffractive optical distance between the two mirrors i.e. $L'^{rt}=2L$, corresponding to the round trip distance the light must travel from the point on the concave input mirror where it enters the cavity, through the cavity to the opposing planar mirror, and thence back through the cavity to the concave input mirror face.

For the configuration shown in FIG. 5, the stability requirement can also be expressed as $0 \leq (1-L'^{rt}/R^1) \leq 1$ where $R^1$ is the radius of curvature of concave input mirror 24 and $^{rt}$ is the round trip diffractive optical distance of beam path 36 commencing with its input at point 24 to its return to point 24 after passage through the flow cell, passage through the prism, reflection by mirror surfaces 26.1 and 26.2 and its second passage through the flow cell.

The photo detector shown as number 20 in the figures and which receives the light emitted from the cavity through, for example mirror 18 in FIG. 2, can be any of the types known in the prior art. Suitable alternatives to a photodiode detector include pyroelectric, bolometer, photocathode, phoromultiplier tube and scintillation detectors. Particularly, when the apparatus of the present invention is used in an ICOS system a suitable detection arrangement is that taught in the Fiedler, et.al. article referred to above, the teaching of which is incorporated herein by reference. The Fiedler et.al design involves a beam splitter which disperses the light emitted from the cavity to a diode array detector.

The invention claimed is:

1. An apparatus for cavity enhanced optical detection comprising:
    a) a source of optical radiation
    b) a resonant optical cavity which provides a round trip path for said optical radiation said cavity comprising:
        i) a plurality of mirrors, a first mirror of said plurality being an input mirror which receives said optical radiation from said source and inputs same into said cavity;
        ii) a flow cell positioned within said cavity, said flow cell comprising at least a first analysis channel which accommodates a flow of analyte fluid there through, the exterior wall of said at least first flow channel closest to said source of optical radiation intersecting said round trip radiation path at an angle approximately equal to Brewster's angle;
        iii) a second mirror of said plurality of mirrors, which second mirror receives the radiation from said optical source after passage of said radiation through both said input mirror and said at least first analysis channel and reflects at least a portion of said received radiation;
    whereby said resonant optical cavity provides a round trip path for analyte fluid having at least two different refractive index values and the location of the point at which said reflected radiation impinges on said input mirror is substantially the same as the point from which said first mirror inputs said radiation into said cavity notwithstanding changes in the refractive index of said analyte fluid or the wavelength of said radiation.

2. The apparatus of claim 1, wherein said first input mirror is concave and said second mirror is substantially planar.

3. The apparatus of claim 1, wherein said flow cell further comprises:
    i) a second analysis channel which second channel intersects said radiation path at an angle which is substantially equal, but opposite to, the angle at which said first analysis channel intersects said radiation path; and
    ii) a fluid inlet channel in fluid communication with both said first and second analysis channels.

4. An apparatus in accordance with claim 1 which also comprises:
    a) a 50/50 beam splitter interposed between said optical source and said input mirror; and
    b) a photo-detector in optical communication with said beam splitter.

5. An apparatus in accordance with claim 1 wherein said optical cavity and said flow cell comprise an integral structure.

6. An apparatus in accordance with claim 1 wherein said optical cavity is a ring resonator which comprises: a concave input mirror and two substantially planar mirrors, said two planar mirrors covering at least a portion of two facets of a triangular prism with said concave input mirror facing the third facet of said prism, and wherein said analysis channel is positioned between said third face and said concave input mirror.

7. An apparatus in accordance with claim 1 wherein said optical radiation is continuous wave.

8. An apparatus in accordance with claim 1 wherein said optical radiation is pulsed.

9. An apparatus in accordance with claim 1 wherein said source of optical radiation is a laser.

10. An apparatus in accordance with claim 1 wherein said source of optical radiation is an incoherent light source.

11. An apparatus in accordance with claim 1 wherein said source of optical radiation is mode match coupled to said resonant cavity.

12. An apparatus in accordance with claim 1 wherein the wavelength of said optical radiation is variable over time.

13. An apparatus in accordance with claim 1 wherein the interior wall surface of said at least one flow channel distal said source of optical radiation intersects said round trip radiation path at an angle approximately equal to Brewster's angle.

14. An apparatus according to claim 1 which also comprises a semi-conductor diode photo detector.

15. An apparatus in accordance with claim 1 wherein said source of optical radiation is broad band and wherein light emitted from said optical cavity is dispersed onto an array detector.

16. An apparatus according to claim 1 wherein said source of optical radiation is broad band and wherein light emitted from said optical cavity is dispersed onto a diode array detector.

17. A cavity ring down spectrometer incorporating the apparatus of claim 1.

* * * * *